(12) United States Patent
Corral et al.

(10) Patent No.: US 8,535,016 B2
(45) Date of Patent: Sep. 17, 2013

(54) HIGH PRESSURE PUMP CONTROL

(75) Inventors: Jose de Corral, Grafton, MA (US); Stanley P. Pensak, Jr., East Walpole, MA (US)

(73) Assignee: Waters Technologies Corporation, Milford, MA (US)

( * ) Notice: Subject to any disclaimer, the term of this patent is extended or adjusted under 35 U.S.C. 154(b) by 1106 days.

(21) Appl. No.: 11/631,354

(22) PCT Filed: Jul. 6, 2005

(86) PCT No.: PCT/US2005/024108
§ 371 (c)(1),
(2), (4) Date: Oct. 22, 2007

(87) PCT Pub. No.: WO2006/017121
PCT Pub. Date: Feb. 16, 2006

(65) Prior Publication Data
US 2008/0206067 A1    Aug. 28, 2008

Related U.S. Application Data

(60) Provisional application No. 60/587,381, filed on Jul. 13, 2004.

(51) Int. Cl.
F04B 49/06 (2006.01)
F04B 49/00 (2006.01)

(52) U.S. Cl.
USPC .......................................... 417/44.2; 417/293

(58) Field of Classification Search
USPC ............................... 417/44.2, 2, 521, 22, 293
See application file for complete search history.

(56) References Cited

U.S. PATENT DOCUMENTS

| | | | |
|---|---|---|---|
| 3,676,020 A | | 7/1972 | Andreasen et al. |
| 4,032,445 A | | 6/1977 | Munk |
| 4,043,906 A | | 8/1977 | Helmer |
| 4,225,290 A | | 9/1980 | Allington |
| 4,406,158 A | | 9/1983 | Allington |
| RE31,608 E | * | 6/1984 | Magnussen, Jr. ............... 417/22 |
| 4,527,953 A | | 7/1985 | Baker et al. |
| 4,627,243 A | * | 12/1986 | Schaub ......................... 62/50.2 |
| 4,629,561 A | | 12/1986 | Shirato et al. |
| 4,714,545 A | * | 12/1987 | Bente et al. ................... 210/101 |

(Continued)

FOREIGN PATENT DOCUMENTS

| | | |
|---|---|---|
| EP | 0183330 A2 | 6/1896 |
| EP | 0309596 A1 | 4/1989 |

(Continued)

OTHER PUBLICATIONS

International Search Report dated Apr. 2, 2007.

(Continued)

*Primary Examiner* — Charles Freay
*Assistant Examiner* — Alexander Comley
(74) *Attorney, Agent, or Firm* — Edwards Wildman Palmer LLP; Nicholas J. DiCeglie, Jr.; George N. Chaclas

(57) ABSTRACT

A feedback control loop for a high pressure pump modifies the accumulator velocity and pressure during solvent transfer. The accumulator velocity is adjusted to maintain the system pressure equal to the expected pressure to thereby eliminate the effect of the flow deficit created by a thermal effect.

8 Claims, 8 Drawing Sheets

(56) References Cited

U.S. PATENT DOCUMENTS

| | | | |
|---|---|---|---|
| 4,808,077 A * | 2/1989 | Kan et al. | 417/2 |
| 4,883,409 A * | 11/1989 | Strohmeier et al. | 417/43 |
| 4,913,624 A * | 4/1990 | Seki et al. | 417/2 |
| 4,919,595 A * | 4/1990 | Likuski et al. | 417/18 |
| 5,062,498 A | 11/1991 | Tobias | |
| 5,108,264 A * | 4/1992 | Abdel-Rahman | 417/20 |
| 5,379,593 A * | 1/1995 | Ishiwata | 60/413 |
| 5,450,743 A * | 9/1995 | Buote | 73/61.56 |
| 5,630,706 A | 5/1997 | Yang | |
| 5,641,270 A * | 6/1997 | Sgourakes et al. | 417/44.2 |
| 5,653,876 A * | 8/1997 | Funke | 210/198.2 |
| 5,882,521 A | 3/1999 | Bouvier et al. | |
| 5,897,781 A * | 4/1999 | Dourdeville | 210/656 |
| 5,969,228 A | 10/1999 | Gorenstein | |
| 6,187,595 B1 | 2/2001 | Staal et al. | |
| 6,312,575 B1 | 11/2001 | Gorenstein | |
| 6,588,254 B1 | 7/2003 | Foster et al. | |
| 6,641,300 B1 | 11/2003 | Lacey et al. | |
| 6,648,504 B2 | 11/2003 | Danley | |
| 6,648,609 B2 * | 11/2003 | Berger et al. | 417/297 |
| 6,726,842 B2 | 4/2004 | Bouvier et al. | |
| 6,736,975 B2 | 5/2004 | Gandelheid et al. | |
| 7,670,480 B2 * | 3/2010 | Witt et al. | 210/101 |
| 2003/0052007 A1 | 3/2003 | Paul et al. | |
| 2004/0018099 A1* | 1/2004 | Berger et al. | 417/313 |
| 2004/0151594 A1 | 8/2004 | Allington et al. | |
| 2004/0232080 A1 | 11/2004 | Neyer et al. | |
| 2006/0219618 A1 | 10/2006 | Witt et al. | |
| 2008/0080981 A1 | 4/2008 | Witt et al. | |
| 2008/0206067 A1 | 8/2008 | De Corral et al. | |

FOREIGN PATENT DOCUMENTS

| | | |
|---|---|---|
| EP | 0471930 A1 | 2/1992 |
| EP | 1707958 | 10/2006 |
| GB | 2433792 B | 7/2007 |
| GB | 2446321 A | 8/2008 |
| WO | WO-03/079000 A1 | 9/2003 |
| WO | WO-2006/017121 A2 | 2/2006 |
| WO | PCT/ISA/210 | 10/2006 |
| WO | WO-2006/103133 | 10/2006 |
| WO | PCT/IB/373 | 10/2007 |

OTHER PUBLICATIONS

Written Opinion of the International Searching Authority dated Apr. 2, 2007.

Web Page—Acquity UPLC, UPLC Systems, Waters Corporation—Jun. 27, 2004.

Web Page—Waters Corporation, HPLC/MS systems, instruments, etc.—Jun. 27, 2004.

Japanese Office Action Mailed Oct. 12, 2010 in Application No. 2007-521505.

Zhou, X., et al., "New Micro-Flow Pumping System for Liquid Chromatography", Journal of Chromatography A, 2001, pp. 165-171.

* cited by examiner

HIGH PRESSURE PUMP CONTROL

RELATED APPLICATIONS

This application is a U.S. national phase application, pursuant to 35 U.S.C. §371, of PCT international application Ser. No. PCT/US2005/024108, filed Jul. 6, 2005, designating the United States and published in English on Feb. 16, 2006 as publication WO 2006/017121A2, which claims priority to U.S. provisional application Ser. No. 60/587,381, filed Jul. 13, 2004. The entire contents of the aforementioned patent applications are incorporated herein by this reference.

BACKGROUND OF THE INVENTION

1. Field of the Invention

The subject invention is directed generally to a scientific laboratory analytical equipment, and more particularly, to analytic equipment with a closed loop feedback controller for a high pressure pump.

2. Background of the Related Art

Scientific laboratories commonly need to separate chemical compounds on such basis as the compounds molecular weight or size, charge or solubility. Separation of the compounds is often a first step in the identification, purification and quantification of the compounds. Chromatography or, more specifically, high performance liquid chromatography (BPLC) has become the analytical tool of choice for applications as varied as biotechnological, biomedical, and biochemical research as well as for the pharmaceutical, cosmetics, energy, food, and environmental industries.

As advances in technology emerge, manufacturers of HPLC instruments are quick to improve the performance of their product lines. In fact, improvements in one technological area or subsystem typically spurn on advancement in interrelated areas or subsystems. U.S. Pat. No. 6,187,595 to Staal, which is incorporated herein by reference in its entirety, discusses several advantages and disadvantages related to evolving approaches based on new technology.

Currently, there are several types of pumps commonly used as subsystems with HPLC instruments. HPLC instruments may incorporate reciprocating pumps, syringe pumps, and constant pressure pumps as are known to those of ordinary skill in the art. For example, most reciprocating pumps include a small motor driven plunger which moves rapidly back and forth in a hydraulic chamber to vary the volume thereof. On the back stroke, the plunger pulls in a solvent. On the forward stroke, the plunger of the reciprocating pump pushes the solvent out to a column. In order to achieve the desired flow stability within the column, multiple plungers are employed, normally two. The two plungers may be employed in series or in parallel to achieve the desired delivery flow and pressure.

During compression of the solvent, energy is absorbed that raises the temperature of the solvent. This thermal effect is proportional to the solvent compressibility, the target pressure (e.g., the desired instrument pressure) and the rate at which the solvent is compressed. For many leading edge technology HPLC instruments, the high pressure and limited amount of time to compress the solvent creates significant thermal effect. The heat is usually dissipated to the surroundings and associated instrument at a rate dependent upon the relative mass and thermal conductivity of the compressed solvent and the surroundings. In most applications, for pressures up to a couple thousand psi, the thermal effects of compression are negligible.

However, the thermal effects at high pressure become more appreciable. The thermal effects create errors in the pressure of the compressed solvent because the solvent temperature is elevated during compression compared with during analysis in the instrument. In other words, just after the solvent is compressed to the target pressure, the pressure decays as the solvent temperature moves toward equilibrium with the instrument. As a result, the compressed solvent settles to a pressure below the target pressure and, thereby, creates a deficit in delivered flow.

Prior art pump control systems lack the required ability to react to the thermal effects of solvent compression at high pressures. So despite the advances of the state of the art, HPLC instruments are lacking in stability and performance. As a result, inaccurate results are still common. Moreover, such prior art instruments are plagued by inadequacies such as complex electronics and numerous additional components that undesirably increase costs and complexity without overcoming the noted drawbacks. In view of the above, it would be desirable to provide a controller for a high pressure pump that affords accurate delivery of the target pressure and the ability to compensate for thermal effects.

SUMMARY OF THE INVENTION

The subject invention provides a controller for a high pressure pump of the series type, wherein the feedback is applied only when the primary plunger delivers flow, just after solvent compression. The feedback ceases when the primary plunger ends flow delivery therefrom, and the pump continues with the normal flow delivery.

It is an object of the present invention to prevent solvent composition errors when the flow from two pumps is used to create a solvent gradient by correcting the delivered flow deficit occurring after solvent compression.

It is understood that this flow deficit is created by adiabatic heating that occurs when the solvent is compressed, and it is proportional to the solvent compressibility, compression pressure, rate at which the solvent is compressed, and thermal mass of the compressed solvent relative to the pump head thermal mass.

It is an object of the present invention to provide a controller for a high pressure pump that uses continuous closed loop feedback on the delivered solvent so that adjustment occurs to maintain the instrument pressure at the target value.

It is an object of the present invention to provide a controller for a high pressure pump that eliminates flow deficits caused by the thermal effects created during compression of the solvent.

It is another object to provide a controller for a high pressure pump that can compensate for thermal effects created during compression of the solvent.

It is still another object to provide a controller for a high pressure pump that achieves quick and accurate response to dynamic flow conditions.

The foregoing objects are achieved by the instant invention which, in one aspect, provides a flow control system for controlling a high pressure pump for delivering a fluid load having a primary piston and an accumulator piston, each piston having a velocity and pressure associated therewith. The flow control system comprises a closed loop feedback control on the accumulator pressure during transfer for modifying the accumulator velocity to maintain a system pressure substantially equal to the expected pressure.

In another aspect, the invention provides a method for controlling an output of a high pressure pump system to reduce an effect created by adiabatic heating, wherein the high pressure pump system includes a primary piston and an accumulator piston, each piston having a velocity and pressure associated therewith. The method comprises the step of modifying the accumulator velocity with a closed loop feedback control on the accumulator pressure during transfer to maintain a system pressure substantially equal to an expected system pressure.

In yet another aspect, the invention provides a method for controlling a velocity of a primary piston in a high pressure pump, wherein an accumulator piston delivers solvent to a system and the primary piston refills the accumulator piston and delivers solvent to the system while the accumulator piston is refilling. The method comprises the step of controlling the velocity of the primary piston before transfer by instructing the primary piston to compress the solvent some time before transfer is due such that adiabatic heating effects extinguish before transfer starts.

In still another aspect, the invention comprises a computer-readable medium whose contents cause a control system to perform a method for controlling an output of a high pressure pump system to eliminate delivery error, wherein the high pressure pump system includes a primary piston and an accumulator piston, each piston having a velocity and pressure associated therewith. The control system has a digital signal processor and a program with functions for invocation by performing the steps of: modifying the accumulator velocity with a closed loop feedback control on the accumulator pressure during transfer to maintain a system pressure substantially equal to an expected system pressure.

Another aspect of the invention provides a method for controlling an output of a high pressure solvent pump system to reduce delivery error, wherein the high pressure pump system includes a primary piston and an accumulator piston, each piston having a velocity and pressure associated therewith. The method comprises the steps of: periodically applying a closed loop feedback control having a closed loop bandwidth to maintain a system pressure substantially equal to an expected system pressure; and filtering the system pressure to eliminate frequencies beyond the closed loop bandwidth.

In another aspect, the invention provides a system for controlling an output of a high pressure pump system to reduce error in solvent delivery. The system comprises a high pressure pump including a primary piston and an accumulator piston, each piston having a velocity and pressure associated therewith; a closed loop feedback control for modifying the accumulator velocity on the accumulator pressure during transfer to maintain a system pressure substantially equal to an expected system pressure; and means for restricting fluid between an outlet of the high pressure pump and a fluid load of the system.

In yet another aspect, the invention provides a method for computing a pressure set point to follow an expected pressure trace in a flow control system for controlling a high pressure pump having a primary piston and an accumulator piston, each piston having a velocity and pressure associated therewith, the flow control system having a closed loop feedback control on the accumulator pressure during a control period for modifying the accumulator velocity to maintain a system pressure substantially equal to the expected pressure. The method comprises the steps of:

computing an initial set point based upon using pressure values immediately before the closed loop feedback control activates;

computing changes to the set point during the control period; performing a prediction of the set point based upon the initial set point and the previous pressure values; and projecting pressure values during the control period to determine the pressure set point.

In still another aspect, the invention provides a flow control system for controlling a high pressure pump having a primary piston and an accumulator piston, each piston having a velocity and pressure associated therewith. The flow control system comprises a closed loop feedback control on the accumulator pressure during a control period for modifying the accumulator velocity to maintain a system pressure substantially equal to the expected pressure.

Another aspect of the invention provides a method for protecting a pump by avoiding a possibility that a pressure control mechanism could command a piston within the pump beyond actual capabilities of the pump. The method comprises the steps of:

computing a volume over a nominal delivery that has been delivered by the pressure control mechanism; and deactivating the pressure control mechanism if the volume delivered exceeds a threshold value.

Yet another aspect of the invention provides a method for isolating a control loop from external fluid conditions such that oscillation from connecting a pair of pumps in parallel is substantially prevented, each pump having a pump cycle, the method comprising the steps of:

interchanging data related to respective positions within a pump cycle between the pair of pumps in order to substantially avoid overlap of respective control periods; and advancing a control period of the pump with longer pump cycle when a control period collision is foreseen to thereby substantially avoid overlap with a control period of the other pump. In one embodiment of this aspect, the method further comprises the steps of:

periodically applying a closed loop feedback control having a closed loop bandwidth to maintain a system pressure substantially equal to an expected system pressure;

filtering the accumulator pressure to eliminate frequencies beyond the closed loop bandwidth;

controlling an output of a high pressure solvent pump system to reduce delivery error, wherein the high pressure pump system includes a primary piston and an accumulator piston, each piston having a velocity and pressure associated therewith; and modifying the accumulator velocity with the closed loop feedback control on the accumulator pressure during transfer.

It should be appreciated that the present invention can be implemented and utilized in numerous ways, including without limitation as a process, an apparatus, a system, a device, a method for applications now known and later developed or a computer readable medium. These and other unique features of the system disclosed herein will become more readily apparent from the following description and the accompanying drawings.

BRIEF DESCRIPTION OF THE DRAWINGS

So that those having ordinary skill in the art to which the subject invention appertains will more readily understand how to make and use the same, reference may be had to the figures wherein.

DETAILED DESCRIPTION OF PREFERRED EMBODIMENTS

The present invention overcomes many of the prior art problems associated with controlling high pressure pumps. The advantages, and other features of the system disclosed herein, will become more readily apparent to those having ordinary skill in the art from the following detailed description of certain preferred embodiments taken in conjunction with the drawings which set forth representative embodiments of the present invention.

Solvent Delivery System Background

Figure 1:
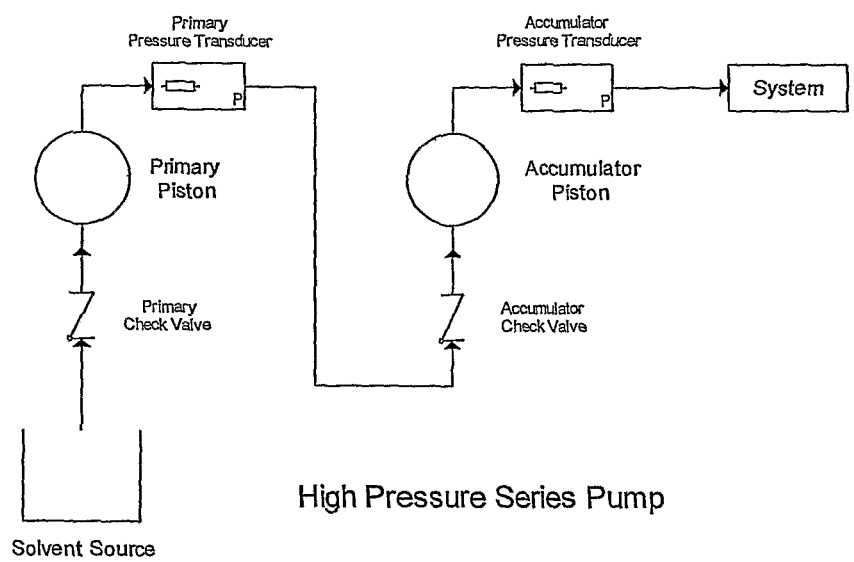
FIG. 1 is a schematic view of a high pressure serial pump constructed in accordance with the subject invention.

Referring to FIG. 1, a schematic view of a high pressure serial pump is illustrated. High pressure pumps for use in chromatography applications normally use a reciprocating type of design involving two pistons. Depending on the fluidic configuration, there are two main design types: parallel or series. In the parallel design, the two pistons alternate in operation whereby one piston delivers flow while the other intakes new solvent from the solvent source. In the series design, only one piston intakes solvent from the solvent source (the primary), while the other (the accumulator) does most of the solvent delivery. The primary takes the responsibility of refilling the accumulator at high pressure when, inevitably, the accumulator needs to intake new solvent.

Preferably, a pressure control algorithm is used in a series pump design; thus for simplicity only the series pump will be covered here.

The primary piston intakes solvent from the solvent source and delivers the solvent to the accumulator piston. The accumulator, then, delivers the solvent to the system. The check valves are passive valves that allow fluid to go in one direction only. Respective pressure transducers measure the pressure at the outlet of each piston. All components are in the same flow path forming a series fluid circuit; thus the name "series". Normally, the plunger size is the same for both pistons.

While the accumulator is delivering flow to the system at high pressure, the primary intakes new solvent from the solvent source and waits until it is time to refill the accumulator. At that point, the primary compresses the solvent to the same pressure measured by the accumulator transducer (the system pressure), and is set ready for delivering to the accumulator. When the accumulator reaches the end of its delivering motion, the pump controller (not shown) instructs the primary to start delivering and the accumulator to start intaking. This operation, known as "transfer", is done at high pressure and continues until the accumulator is completely full and ready to resume its normal delivery.

While transfer is taking place, the accumulator is, obviously, not delivering to the system. Therefore, the primary has to take over that responsibility in order to avoid interruption in the flow delivered to the system. To accomplish this task, transfer is done at a much higher plunger velocity than the accumulator's normal delivery velocity, and a portion of the primary delivery goes to the system.

Once transfer is finished, the pump controller instructs the accumulator to resume normal delivery, and the primary to intake new solvent. This cycle, known as the "pump cycle", repeats continuously while the pump is delivering solvent to the system. The pump cycle duration depends mainly on the stroke volume and the delivered flow. The roll of the check valves is easy to understand. The primary check valve allows the primary to intake solvent at atmospheric pressure from the solvent source, but prevents the solvent from going back to the solvent container when the primary compresses the solvent to the system pressure. The accumulator check valve allows the primary to deliver solvent to the accumulator, but prevents the accumulator delivery at high pressure from going back to the primary when the primary is intaking new solvent at atmospheric pressure.

Figure 2:
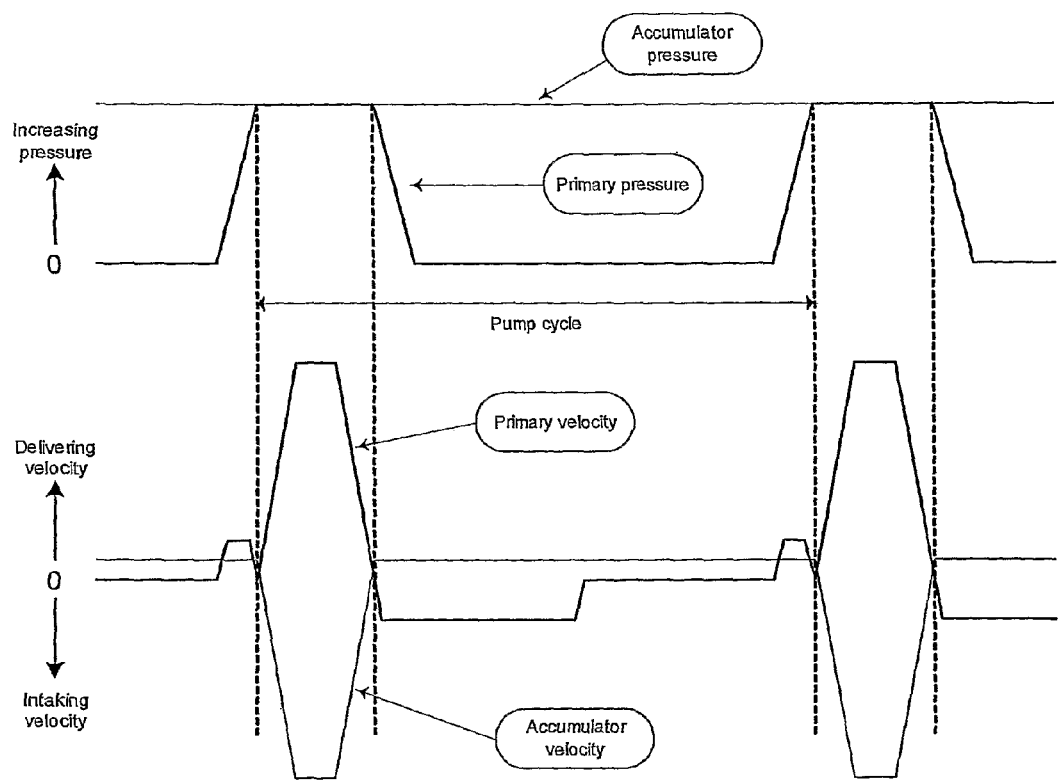
FIG. 2 illustrates typical profiles of velocity and pressure in both pistons, during an entire pump cycle of a preferred embodiment.

The accumulator pressure transducer measures the system pressure, and provides the input to the pressure control algorithm. The accumulator also provides the target compression pressure to the primary, when the primary starts the compression of new solvent. The primary pressure transducer measures the pressure inside the primary, so the compression is stopped when the pressure reaches the compression target. Referring to FIG. 2, typical profiles of velocity and pressure in both pistons, during an entire pump cycle is shown.

High Pressure Compression Effects

When the solvent inside the primary is compressed, its temperature rises. This temperature increase, known as adiabatic heating, is lost to the solvent surroundings and to the system (when the primary starts delivering), at a rate dependent on the relative mass and thermal conductivity of the compressed solvent and the surroundings. However, this temperature increase creates an error in the pressure of the compressed solvent, because the solvent temperature at the time of compression is higher than the temperature the solvent will eventually have (the temperature of the system).

Therefore, just after the solvent is compressed to the target pressure (the system pressure), its pressure starts to decay as its increased temperature starts to be equilibrated to the system temperature. The compressed solvent pressure eventually settles at a value below the intended system pressure. This creates a deficit in delivered flow when the primary starts delivering.

The thermal effect is proportional to the solvent compressibility, to the compression pressure (the system pressure), and to the rate at which the solvent is compressed. For pressures up to a few thousand psi this thermal effect can normally be ignored, but it is significant at higher pressures. Furthermore, due to the timing involved in the reciprocating pumps' action, there is normally a limited amount of time to compress the solvent from atmospheric pressure to system pressure. Therefore, this thermal effect creates significant flow delivering errors, which represent solvent composition errors when the solvents of two pumps are combined together at high pressure to form a solvent gradient.

Pressure Control Description

Figure 3:
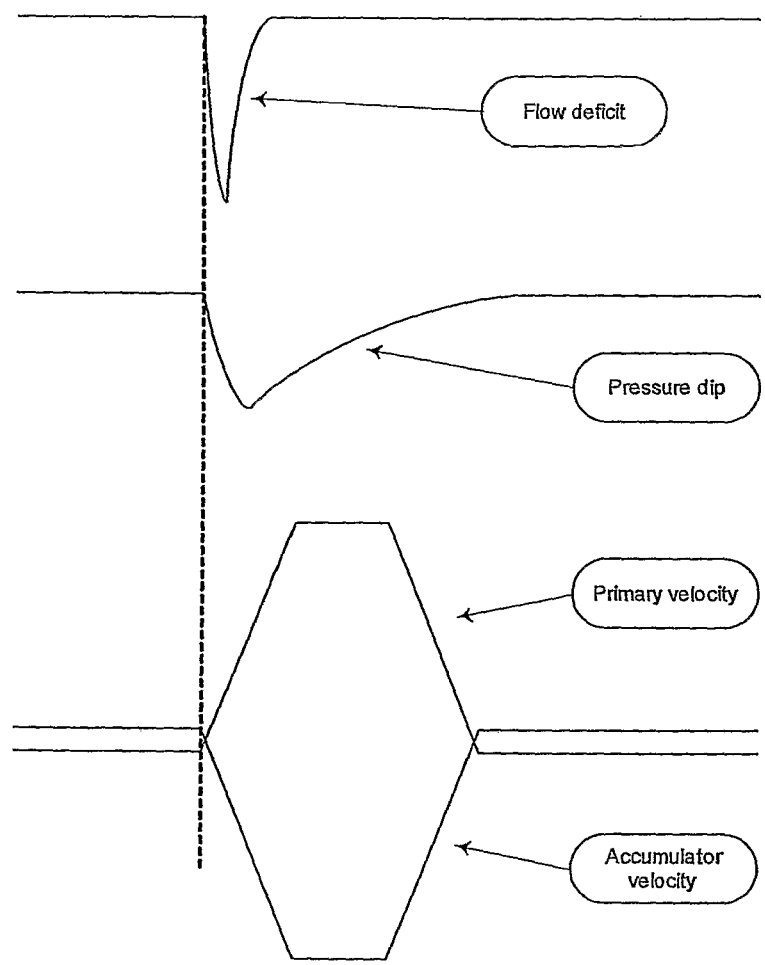
FIG. 3 illustrates an example of the flow deficit and the correspondent pressure dip, relative to the velocity profiles during transfer of a preferred embodiment.

Referring to FIG. 3, an example of the flow deficit and the correspondent pressure dip, relative to the velocity profiles during transfer is shown. As the primary is where the adiabatic heating effect takes place, the flow deficit occurs when the primary enters in fluid communication with the accumulator. Up to that point, the pump flow is correct, as the pump flow is delivered by the accumulator only.

The flow deficit shows up as a pressure dip and is sensed by the accumulator pressure transducer. As the fluidic dynamics affects the measured pressure, the pressure dip profile does not necessarily match the flow deficit profile. They would only match if the time constant of the fluidics is smaller than the time constant of the flow deficit (small fluidic capacitance or small fluidic resistance).

The flow deficit duration varies mainly with pressure and solvent compressibility and normally lasts for a period shorter than transfer, although the flow deficit duration could extend beyond the duration of transfer.

Figure 4:
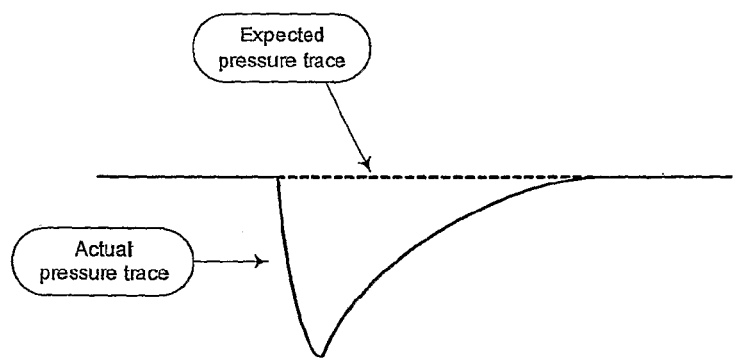
FIG. 4 illustrates the difference between the expected and actual accumulator (system) pressure traces of a preferred embodiment.
Figure 5:
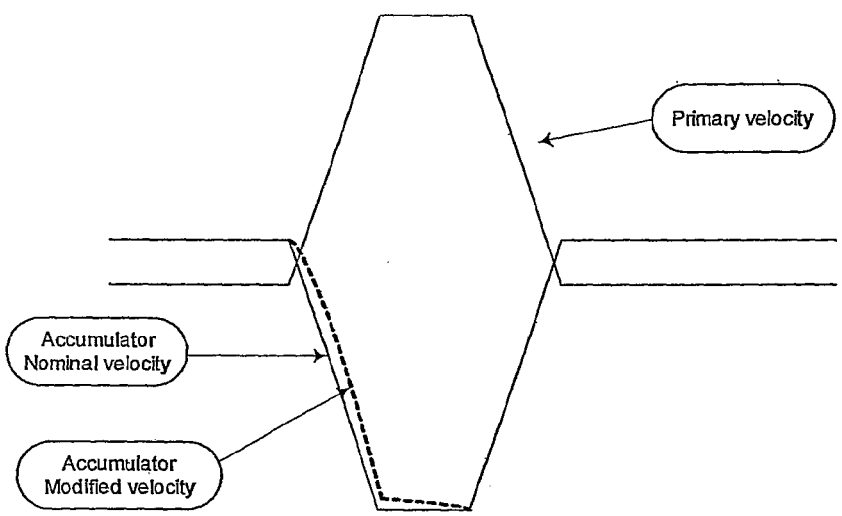
FIG. 5 shows how the accumulator velocity is modified during the flow deficit, from its nominal velocity profile of a preferred embodiment.

Referring to FIG. 4, the difference between the expected and actual accumulator (system) pressure traces is shown. To compensate for this error, the accumulator velocity is modified during the flow deficit, from its nominal velocity profile, as shown in FIG. 5. The modification of the accumulator velocity is done with a closed loop feedback control on the accumulator pressure during transfer. The accumulator velocity is adjusted to maintain the system pressure equal to the expected pressure. This eliminates the effect of the flow deficit created by the thermal effect.

As mentioned above, the pressure control runs when the primary is delivering (during transfer), and ceases when the primary ends its delivery. Once transfer is finished, the pump continues with the normal accumulator delivery. Therefore, the feedback control is applied only once per pump cycle. The feedback control does not run continuously, i.e., the feedback control can be turned on before transfer, and turn off after transfer.

The intermittent use of the feedback control yields improved delivery accuracy. Preferably, the feedback control is only utilized enough to achieve the desired accuracy. During transfer, as the figures above show, the accumulator nominal velocity profile is set by the pump controller, and it is substantially a mirror image of the primary velocity profile. The pressure control algorithm adjusts the accumulator velocity on top of this nominal velocity profile, unaware that the pump controller is modifying the accumulator velocity too. The pressure control does not modify the primary velocity.

Pressure Control Algorithm
Pressure Filter

Before using the measured pressures for pressure control, they should be filtered to eliminate frequencies beyond the closed loop bandwidth. If these frequencies are too close to a multiple of the loop sampling frequency, the frequencies could alias into the control bandwidth, creating unexpected loop behavior.

The main source of high frequency components in the measured pressures is the resonance of the pump motors, which is about 200 Hz. There is also high frequency noise associated with the pressure transducers. The electronic two pole Butterworth filter at 225 Hz, located just before the analog to digital (A/D) conversion, does not filter these frequencies enough.

A software digital filter running in the pump controller digital signal processor (DSP) issued to remove the high frequencies in the measured pressures.

The filter runs at the A/D converter rate (2.441 KHz), and is made of two cascaded single pole IIR filters at 100 Hz, followed by a sync filter (FIR filter) that averages the last 12 samples. The sync filter effectively removes most of the motor resonance frequency. The filter creates a lag of about 5 milliseconds.

Control Start And End Points

In a preferred embodiment, the pressure control occurs advantageously during transfer. In alternative embodiments, the period of pressure control may be longer or shorter than transfer. For example, the pressure control may start before transfer begins, and extends until sometime after transfer is finished. The start point is set at the point when the primary starts to compress the solvent, and the end point is about 50 milliseconds after the solvent inside the primary has been decompressed. This extended control period allows compensation for other flow delivery errors that occur around transfer, due to mechanical imperfections and the like.

Fluidic Isolation

In order to make the feedback control loop work optimally under different fluid load conditions, it is desirable to add a small amount of fluid restriction between the outlet of the pump and the system fluid load. In a preferred implementation, this fluid restriction is created with 12" of 0.005" inner diameter (ID) tubing. This decouples the dynamic load seen by the feedback loop from the external fluid capacitance, which, otherwise, would need to be computed for each load condition.

This fluid restriction also helps isolate the effect that one pump creates on the other, when two pumps are connected in parallel to form high pressure solvent gradients. Without isolation restrictions, the feedback control loop would oscillate when the control periods of both pumps overlap. This is because both pumps would try to compensate the same pressure, which is created by contributions from both pumps. Each control loop would not know which is the portion it has to compensate.

The isolation restrictors allow each control loop to get a pressure measurement that is dominated by its own contribution, although it contains some amount created by the other pump. The restrictors along with the system fluid capacitance create enough isolation at the loop crossover frequency, sufficient to prevent oscillation.

Pressure Set point Computation

Another element of this control algorithm is the computation of the correct control loop set point at any given time during the control period. The pressure set point is not necessarily constant during the entire control period. Actually, the pressure set point should follow the expected pressure trace that would have been if the pressure dip was not present.

The pressure set point algorithm computes the initial set point and how the actual set point changes during the control period, using the pressure values immediately before the control starts. The pressure set point algorithm does a linear prediction with these pressure values, and projects the pressure values during the control period. These projected values are used as the pressure set point. A linear prediction has proved to be sufficient when the control period is less than one second. However, curved prediction methods could be used as well, such as a quadratic fit.

Figure 6:
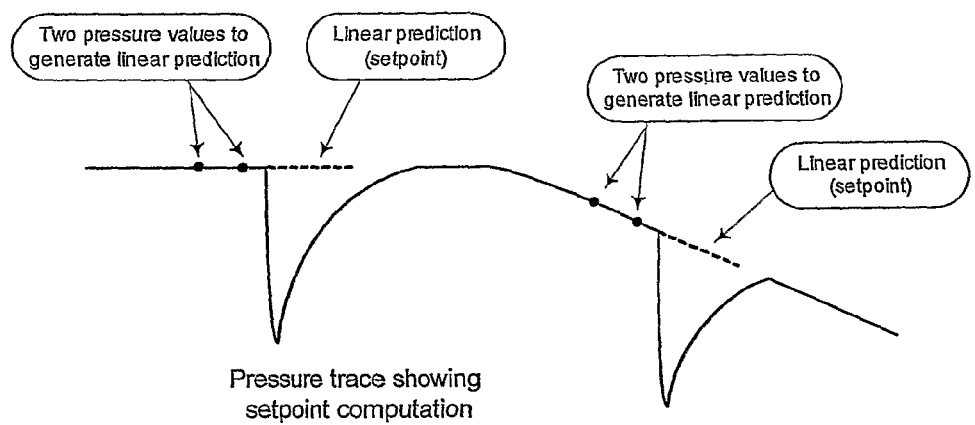
FIG. 6 shows an example of how a linear prediction is used to compute the pressure set point based on two pressure values just before the start of control of a preferred embodiment.

FIG. 6 shows an example of how a linear prediction is used to compute the pressure set point based on two pressure values just before the start of control. The two pressure values are used to generate a straight line that determines the set point values. The figure shows two cases, one with a horizontal prediction, and the other with a sloped prediction.

The set point algorithm uses a strongly filtered version of the pressure to perform the linear prediction. This digital filter provides the trend of the pressure, and prevents local noisy pressure samples from affecting the correct set point or set point slope computation. This digital filter is a single pole low pass filter with a corner frequency that varies with the set-flow, between 10 Hz for the highest flow, and 0.01 Hz for the lowest flow.

The algorithm also takes into account the set-flow changes, in order to compute the correct set point slope under varying fluid load conditions.

Feedback Control Loop

The pressure feedback control is designed as a proportional-integral-derivative (PID) control loop. The inputs are the pressure set point and the filtered accumulator pressure, and the output is the accumulator velocity. The loop sampling frequency is set to 200 Hz.

Figure 7:
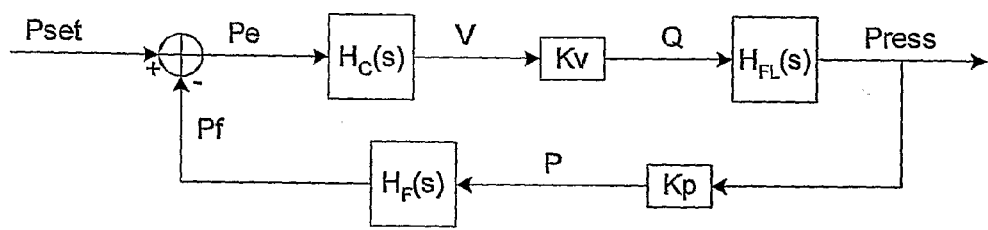
FIG. 7 illustrates a simplified block diagram of the control loop of a preferred embodiment.

A simplified block diagram of the control loop is shown in FIG. 7 with Table 1 serving as a legend.

TABLE 1

| | | |
|---|---|---|
| Press | Actual pressure | (psi) |
| Kp | Conversion constant: actual pressure to measured pressure | (counts)/(psi) |
| P | Measured pressure | (counts) |
| HF(s) | Filter transfer function | |
| Pf | Filtered pressure | (counts) |
| Pset | Pressure set point (expected pressure without the pressure dip) | (counts) |
| Pe | Pressure error | (counts) |
| HC(s) | Compensation transfer function | |
| V | Accumulator velocity | (steps/sec) |
| KV | Conversion constant: velocity to flow | (ml/min)/(steps/sec) |
| Q | Actual delivered flow | (ml/min) |
| HFL(s) | Fluidics transfer function | |

The formulas based upon this exemplary embodiment are as follows:

$$Kp = 2.64254 \left(\frac{counts}{psi}\right)$$

$$H_F(\omega) = \frac{1}{(1.59 \cdot 10^{-3} \cdot j\omega + 1)^2} \cdot \frac{1 - \exp\left(-j\omega \cdot \frac{12}{\omega_s}\right)}{1 - \exp\left(-j\omega \cdot \frac{1}{\omega_s}\right)} \left(\frac{counts}{counts}\right)$$

$$\omega_s = 15337 \text{ (rad/sec)} = \text{filter sampling frequency}$$

$$H_C(s) = Kc \frac{(\tau_1 s + 1) \cdot (\tau_2 s + 1)}{s} \left(\frac{steps/sec}{counts}\right)$$

$Kc$ = compensation gain $\tau_1$ = first compensation zero time constant $\tau_2$ = second compensation zero time constant $$Kv = 2.3538 \cdot 10^{-4} \left(\frac{ml/min}{steps/sec}\right)$$

$$H_{FL}(s) = \frac{(\tau_F s + 1) \cdot R_i + R_F}{(\tau_F \cdot \tau_i)s^2 + (\tau_F + \tau_i + \tau_c)s + 1} \left(\frac{psi}{ml/min}\right)$$

$$\tau_F = R_F C_F$$

$$\tau_i = R_i C_H$$

$$\tau_c = R_F C_H$$

$R_F$ = fluid load resistance $C_F$ = fluid load capacitance $R_i$ = fluid isolation resistance $C_H$ = fluid pump head capacitance For the typical fluid conditions, the loop crossover frequency is 14 Hz with a phase margin of 61 degrees, and a settling time of 56 milliseconds. This loop behavior does not change much for a wide range of fluid conditions.

The fluid pump head capacitance is a gain term in the loop, and its value is determined for each type of solvent being used. This capacitance is computed in the primary when the solvent is compressed to the target pressure.

Feed Forward Compensation

This step of the control algorithm intends to compensate for pressure errors with frequencies beyond the loop crossover frequency, such as those created by certain types of check valves. These pressure disturbances are too fast and the control loop cannot compensate for them.

First, the high frequency components of the pressure are separated using a digital high pass filter with a corner frequency above the loop crossover frequency. Then, an additional compensation velocity is added to the accumulator velocity, computed as follows.

The feed forward accumulator velocity contribution is a factor of the set-velocity. This factor is inversely proportional to the ratio of the high frequency pressure components and the pressure set point.

Control Guard

This is a protection algorithm to avoid the possibility that the pressure control commands an accumulator velocity or position beyond the actual capabilities of the pump mechanics.

In this regard, an important control situation is the section between the start of control, and the start of transfer. At this point, the accumulator is near the end of its possible displacement, and any exaggerated velocity increase requested by the control loop will most likely result in the accumulator plunger hitting the hardware stop. For example, an air bubble entering the pump is a typical scenario that could lead to this situation. The pressure control will increase the accumulator velocity substantially trying to compress the bubble.

This is not the case once transfer has started, because the pump controller has initiated the-accumulator intake. The intake velocity is higher than the highest possible velocity set by the control loop, so it is not possible for the plunger to hit the hardware stop.

The control guard algorithm computes the volume over the nominal delivery that has been delivered by the control loop so far, and turns the control off if the volume delivered exceeds a reasonable threshold value.

Two Pump Control Collision Avoidance

The isolation restrictors, discussed above, isolate the control loop from external fluid conditions, and prevent the control loop from oscillating when two pumps connected in parallel overlap their control periods. However, this isolation is not enough for high precision solvent gradients, where the small remaining interaction between both pump's control loops creates solvent composition errors.

To eliminate these errors, the two pumps interchange information about their respective position within the pump cycle, in order to avoid the control periods overlapping. In other words, each pump knows the other pump's cycle duration and current position within that cycle.

When a control period collision is foreseen, the pump with longer pump cycle advances its control period just enough to avoid the overlap with the other pump control period. This technique effectively removes any remaining composition errors in solvent gradients.

Alternative Pressure Control Embodiment

In another embodiment, the pressure control algorithm is based on controlling the primary velocity before transfer, rather than the accumulator velocity during transfer. The nominal primary velocity profile is changed slightly.

In the standard serial pump design, as described above, the primary does not compress the solvent until transfer is just about to occur. When the primary compresses the solvent, the adiabatic heating effect takes place, and transfer starts. This is the reason why the flow deficit occurs during transfer.

Figure 8:
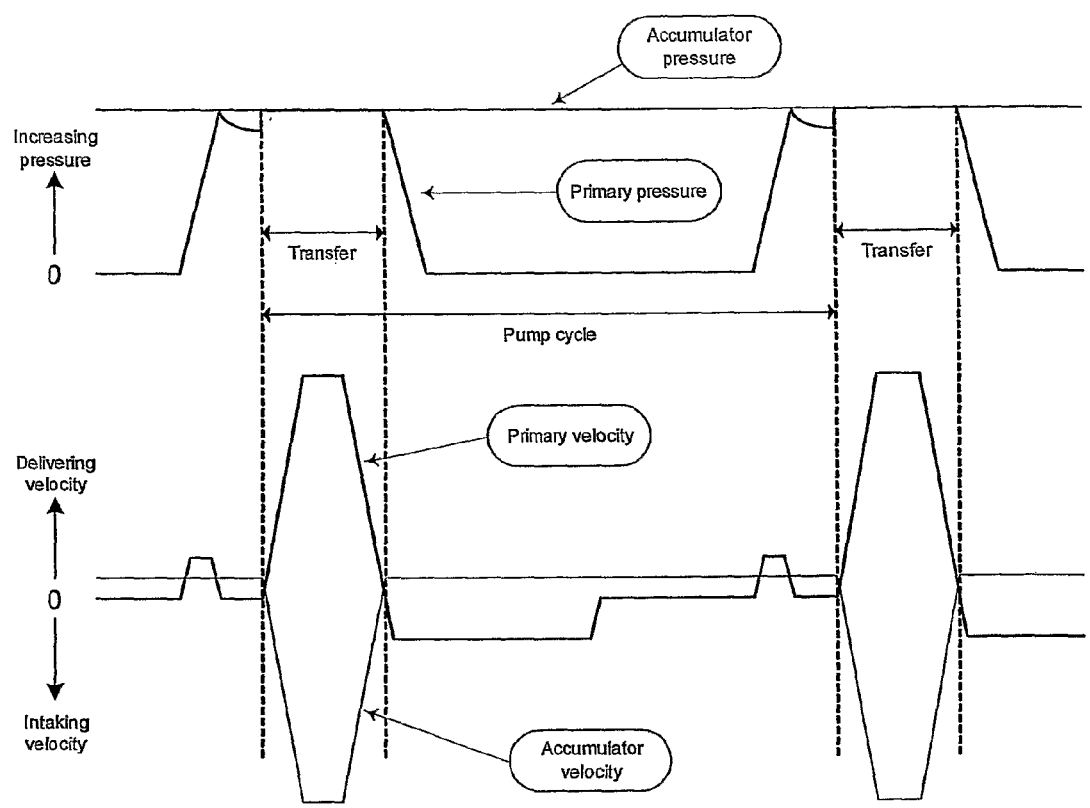
FIG. 8 illustrates typical profiles of velocity and pressure in both pistons, during an entire pump cycle of another preferred embodiment.

However, the primary can be instructed to compress the solvent some time before transfer is due, to let the adiabatic heating effect extinguish by the time transfer starts. FIG. 8 shows the pressure and velocity profiles with this change (compare with similar FIG. 2).

FIG. 8 shows how the adiabatic heating effect creates a pressure decay on the primary pressure just after compression. This pressure decay will create a flow deficit on the delivered flow when transfer starts.

This alternative control approach deals with the adiabatic heating effect problem by controlling the primary pressure between the end of compression and the start of transfer. The pressure control adjusts the primary velocity to maintain the primary pressure slightly below the accumulator pressure.

Figure 9:
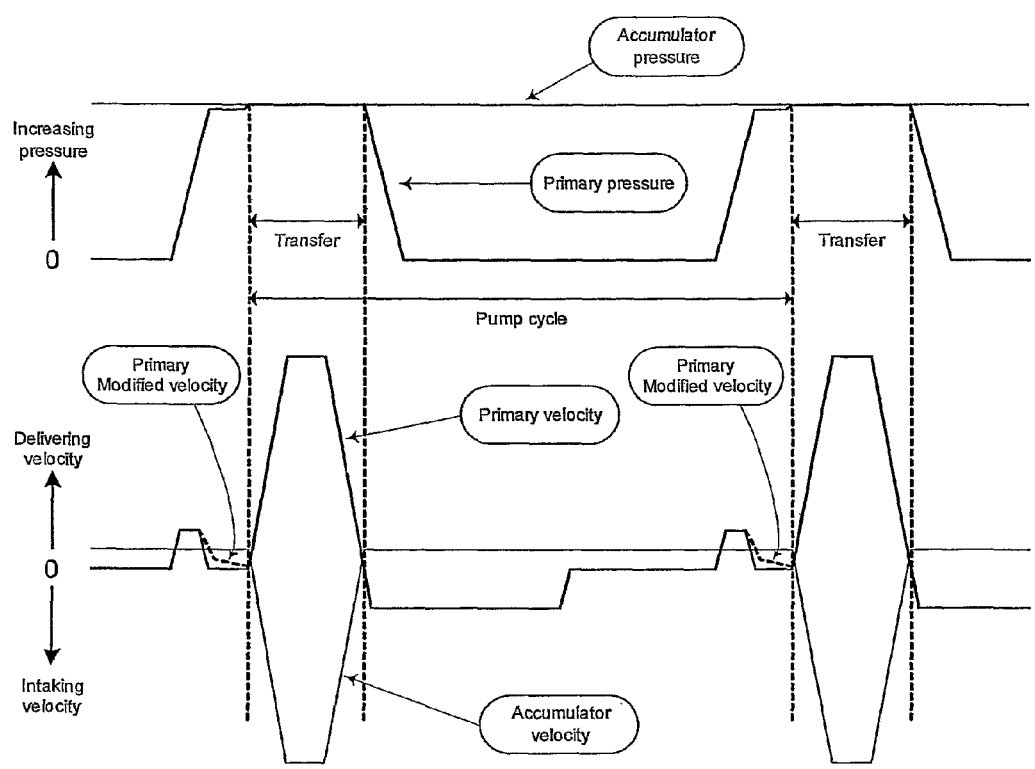
FIG. 9 illustrates the effect of the pressure control on the primary pressure, and how the primary velocity is modified by the control loop.

This compensates for the adiabatic heating effect and leaves the primary pressure at the right value when transfer starts. The primary pressure should be maintained below the accumulator pressure to guarantee that the accumulator check valve stays closed during the primary pressure control. Referring now to FIG. 9, the effect of the pressure control on the primary pressure, and how the primary velocity is modified by the control loop are shown.

There are inherent advantages of this alternative control approach. An advantage is that the system is not affected by external fluidic conditions, such as the fluidic load, or the transfer overlap of a second pump connected in parallel. As the accumulator check valve stays closed during the control period, the primary pressure is not affected by anything happening downstream of the accumulator check valve. Also, there is no need for a set point computation algorithm, because the accumulator pressure determines the set point value.

In regard to disadvantages, this control alternative provides compensation for the adiabatic heating effect only, and not for the mechanical imperfections that affect transfer, for which the other control algorithm compensates for.

Incorporation by Reference

All patents, published patent applications and other references disclosed herein are hereby expressly incorporated herein in their entireties by reference.

Equivalents

Although the subject invention has been described with respect to preferred embodiments, those skilled in the art will readily appreciate that various changes and/or modifications can be made to the invention without departing from the spirit or scope of the invention.

What is claimed is:

1. A flow control system for delivering a fluid in a chromatography apparatus comprising:
   a high pressure pump including: a primary piston for intaking a fluid from a fluid source; and an accumulator piston for receiving the fluid from the primary piston and delivering the fluid in the chromatography apparatus, each piston having a velocity and pressure associated therewith, wherein during a transfer portion of a pump cycle of the high pressure pump, the primary piston refills the accumulator piston and delivers the fluid to the chromatography apparatus; and
   an instantaneous closed loop feedback control only on the accumulator pressure substantially only during the transfer portion for modifying the accumulator velocity to maintain a system pressure substantially equal to an expected pressure to substantially eliminate an effect created by adiabatic heating at high pressure,
   wherein during the transfer portion, a nominal accumulator piston velocity profile has an initial linear descending portion, a second steady state portion, and a third linear ascending portion, and the instantaneous closed loop feedback control only modifies the initial linear descending portion and the second steady state portion.

2. A flow control system as recited in claim 1, further comprising an isolation restrictor connected between an output of the accumulator piston and a system fluid load.

3. A flow control system for controlling a high pressure pump having a primary piston and an accumulator piston, each piston having a velocity and pressure associated therewith, the flow control system comprising an instantaneous continuous closed loop feedback control only on the accumulator pressure only during a control period in which the control period is less than a pump cycle, wherein the instantaneous closed loop feedback control modifies the accumulator velocity to maintain a system pressure substantially equal to an expected pressure,
   wherein during transfer, a nominal accumulator piston velocity profile has an initial linear descending portion, a second steady state portion, and a third linear ascending portion, and the instantaneous continuous closed loop feedback control only modifies the initial linear descending portion and the second steady state portion.

4. A flow control system as recited in claim 3, wherein the control period is substantially equal to a transfer time in which the accumulator piston performs fluid intake.

5. A flow control system as recited in claim 3, wherein the control period is longer than a transfer time in which the accumulator piston performs fluid intake.

6. A flow control system as recited in claim 3, wherein the control period is shorter than a transfer time in which the accumulator piston performs fluid intake.

7. A high pressure pump having a flow control system for controlling delivery of a fluid at a target pressure to a chromatography apparatus comprising:
   an accumulator piston for delivering the fluid to the chromatography apparatus;
   an accumulator sensor for reading a pressure of fluid output by the accumulator piston;
   a primary piston for intaking the fluid from a source and delivering the fluid to the accumulator piston, each piston being a same capacity and having a velocity and pressure associated therewith, wherein during a transfer portion of a pump cycle, the primary piston refills the accumulator piston and delivers the fluid to the chromatography apparatus and a nominal accumulator piston velocity profile and a nominal primary piston velocity profile are substantially mirror images during the transfer portion; and
   a primary sensor for reading a pressure of fluid output by the primary piston; and
   an instantaneous closed loop feedback control operatively connected to the pistons and sensors for substantially eliminating an effect created by adiabatic heating related to the primary piston by being on substantially only during the transfer portion to increase only the accumulator piston velocity during the transfer portion to maintain a system pressure substantially equal to the target pressure,
   wherein during transfer, the nominal accumulator piston velocity profile has an initial linear descending portion, a second steady state portion, and a third linear ascending portion, and the closed loop feedback only modifies the initial linear descending portion and the second steady state portion.

8. A high pressure pump as recited in claim 7, wherein the accumulator piston velocity profile is modified based upon the target pressure and the fluid.

* * * * *